US012618105B2

(12) United States Patent
Dai et al.

(10) Patent No.: US 12,618,105 B2
(45) Date of Patent: May 5, 2026

(54) COMPOSITION, REACTION LIQUID AND METHOD FOR IMPROVING QPCR TEST PERFORMANCE, AND USE THEREOF

(71) Applicant: SANSURE BIOTECH INC., Changsha (CN)

(72) Inventors: Lizhong Dai, Changsha (CN); Bozhi Ji, Changsha (CN); Kang Wu, Changsha (CN); Jia Liu, Changsha (CN); Zhongping Deng, Changsha (CN); Weimin Miao, Changsha (CN)

(73) Assignee: Sansure Biotech Inc., Changsha (CN)

( * ) Notice: Subject to any disclaimer, the term of this patent is extended or adjusted under 35 U.S.C. 154(b) by 877 days.

(21) Appl. No.: 17/936,128

(22) Filed: Sep. 28, 2022

(65) Prior Publication Data

US 2023/0193369 A1     Jun. 22, 2023

Related U.S. Application Data

(63) Continuation of application No. PCT/CN2020/121056, filed on Oct. 15, 2020.

(30) Foreign Application Priority Data

Apr. 23, 2020    (CN) .......................... 202010326989.0

(51) Int. Cl.
*C12Q 1/68*        (2018.01)
*C12Q 1/6851*     (2018.01)

(52) U.S. Cl.
CPC ................................. *C12Q 1/6851* (2013.01)

(58) Field of Classification Search
CPC .. C12Q 1/6851; C12Q 1/6844; C12Q 1/6846; C12Q 1/6848
See application file for complete search history.

(56) References Cited

FOREIGN PATENT DOCUMENTS

| | | |
|---|---|---|
| CN | 1464070 A | 12/2003 |
| CN | 1940087 A | 4/2007 |
| CN | 1981055 A | 6/2007 |
| CN | 100475976 C | * 4/2009 |
| CN | 103409540 A | 11/2013 |
| CN | 104830841 A | 8/2015 |
| CN | 105112559 A | 12/2015 |
| CN | 105378075 A | 3/2016 |
| CN | 105392363 A | 3/2016 |
| CN | 106755414 A | 5/2017 |
| CN | 108570498 A | 9/2018 |
| CN | 108728518 A | 11/2018 |
| CN | 108913758 A | 11/2018 |
| CN | 109402240 A | 3/2019 |
| CN | 110527747 A | 12/2019 |
| CN | 110945142 A | 3/2020 |
| CN | 111218502 A | 6/2020 |
| WO | 2008090340 A2 | 7/2008 |
| WO | 2014131906 A1 | 9/2014 |
| WO | 2016176322 A1 | 11/2016 |
| WO | 2018113351 A1 | 6/2018 |
| WO | 2020005019 A1 | 1/2020 |

OTHER PUBLICATIONS

CNIPA First Office Action for Application No. CN202010326989.0; issued on Apr. 4, 2007.
Supplementary European Search Report for application No. EP20931793; issued on Oct. 27, 2022.
Shi Xiaofeng et al.; Optimization of Detecting Methods for Norovirus on Blueberries and Application in Fruits and Vegetables; Journal of Chinese Institute of Food Science and Technology; Dec. 2018; vol. 18 No. 12 (abstract only in English).
PCT International Search Report for Application No. PCT/CN2020/121056; issued Jan. 26, 2021.
PCT Written Opinion of the International Search Authority for Application No. PCT/CN2020/121056.

* cited by examiner

*Primary Examiner* — Jezia Riley
(74) *Attorney, Agent, or Firm* — Flener IP & Business Law

(57)                ABSTRACT

A composition for improving the detection performance of fluorescent quantitative PCR. The composition comprises bovine serum albumin, sorbitol, ammonium sulfate, formamide, tetramethylammonium chloride, and at least one of dithiothreitol and betaine. The present invention further relates to a qPCR reaction liquid containing the composition and a preparation method therefor. The composition can improve the sensitivity, specificity, and interference resistance of real-time fluorescent quantitative PCR.

15 Claims, 1 Drawing Sheet

Specification includes a Sequence Listing.

SEQUENCE LISTING

```
Sequence total quantity: 3
SEQ ID NO: 1            moltype = DNA   length = 18
FEATURE                 Location/Qualifiers
source                  1..18
                        mol_type = other DNA
                        note = Forward primer sequence
                        organism = synthetic construct
SEQUENCE: 1
gcggacatgg aggacgtg                                              18

SEQ ID NO: 2            moltype = DNA   length = 19
FEATURE                 Location/Qualifiers
source                  1..19
                        mol_type = other DNA
                        note = Reverse primer sequence
                        organism = synthetic construct
SEQUENCE: 2
gctgcccatc tcctccatc                                             19

SEQ ID NO: 3            moltype = DNA   length = 23
FEATURE                 Location/Qualifiers
source                  1..23
                        mol_type = other DNA
                        note = Taqman probe sequence
                        organism = synthetic construct
SEQUENCE: 3
cttctgcagg tcatcggcat cgc                                        23
```

COMPOSITION, REACTION LIQUID AND METHOD FOR IMPROVING QPCR TEST PERFORMANCE, AND USE THEREOF

CROSS-REFERENCE TO RELATED APPLICATIONS

This application is a continuation of International Application No. PCT/CN2020/121056, filed on Oct. 15, 2020, which claims priority to Chinese Patent Application No. 202010326989.0, filed on Apr. 23, 2020. The disclosures of the aforementioned applications are hereby incorporated by reference in their entireties.

TECHNICAL FIELD

The present invention belongs to the field of molecular biology detection, in particular to a composition, a kit, and a method for improving PCR detection performance, and more particularly to the improvement of sensitivity, specificity, and interference resistance of fluorescent quantitative PCR.

BACKGROUND

Real-time fluorescent quantitative PCR (quantitative real-time PCR) is a method for measuring the total amount of a product after each polymerase chain reaction (PCR) cycle with a fluorescent chemical in a nucleic acid amplification reaction. It is a method for quantitative analysis of a specific DNA sequence in a sample under test by an internal reference or external reference method. Real-time PCR is real-time detection of a PCR process by fluorescence signals during PCR amplification. The Ct value of a template has a linear relationship with an initial copy number of the template during an exponential period of the PCR amplification, which thus becomes a basis for quantification. Fluorescent indicators for qPCR detection are mainly divided into two categories: one is fluorescent probes, such as Taqman probes and molecular beacon probes; the other is fluorescent dyes that can bind to a double-stranded DNA, such as SYBR Green and EvaGreen. Technologies for improving the detection performance of real-time fluorescent quantitative PCR discussed herein mainly involve improvement of the qPCR detection performance of a fluorescent probe method, especially a Taqman probe method.

There are many factors affecting the qPCR detection performance, and many studies have so far focused on the improvement of qPCR detection effects. For example, Chinese Patent CN1981055A mentioned the application of a mixture containing a polynucleotide polymerase to improve the stability of a PCR reaction liquid; for another example, Chinese Patent CN103409540A mentioned the use of a novel dye Gelgreen I combined with a Taq enzyme to improve and optimize the amplification efficiency of qualitative PCR; for still another example, Chinese Patent CN1464070A mentioned the use of gold nanoparticles with different particle sizes as an identification amplifier of a DNA detector to improve the detection sensitivity in DNA detection.

However, in the field of qPCR detection, there is currently a lack of a simple and convenient solution that can simultaneously improve various aspects of qPCR detection performance, including but not limited to detection sensitivity, interference resistibility, detection specificity, and the like, of DNA/RNA amplification.

SUMMARY

In view of this, in a first aspect, the present invention provides a composition for improving qPCR detection performance, the composition comprising:

bovine serum albumin, sorbitol, ammonium sulfate, formamide, and tetramethylammonium chloride, and at least one of dithiothreitol and betaine.

In a particular embodiment, the composition comprises bovine serum albumin, dithiothreitol, sorbitol, ammonium sulfate, formamide, and tetramethylammonium chloride.

In a particular embodiment, the composition comprises bovine serum albumin, sorbitol, betaine, ammonium sulfate, formamide, and tetramethylammonium chloride.

In a particular embodiment, the composition comprises bovine serum albumin, dithiothreitol, sorbitol, betaine, ammonium sulfate, formamide, and tetramethylammonium chloride.

In the present invention, the bovine serum albumin has a final concentration of 10-150 µg/mL, preferably 80-120 µg/mL in the qPCR reaction liquid, for example, 70 µg/mL, 75 µg/mL, 80 µg/mL, 85 µg/mL, or 90 µg/mL, more preferably, a final concentration of 80 µg/mL.

In the present invention, the dithiothreitol has a final concentration of 1-10 mM, preferably 2-8 mM in the qPCR reaction liquid, for example, 2 mM, 4 mM, 6 mM, or 8 mM, more preferably, a final concentration of 3 mM.

In the present invention, the sorbitol has a final concentration of 1-10 w/v %, preferably 4-6 w/v % in the qPCR reaction liquid, for example, 4 w/v %, 5 w/v %, or 6 w/v %, more preferably, a final concentration of 4 w/v %.

In the present invention, the betaine has a final concentration of 0.5-4 mol/L, preferably 0.6-1 mol/L in the qPCR reaction liquid, for example, 0.6 mol/L, 0.7 mol/L, 0.8 mol/L, or 0.9 mol/L, more preferably, a final concentration of 0.8 mol/L.

In the present invention, the ammonium sulfate has a final concentration of 2-50 mM, preferably 8-15 mM in the qPCR reaction liquid, for example, 8 mM, 9 mM, 10 mM, 11 mM, or 12 mM, more preferably, a final concentration of 10 mM.

In the present invention, the formamide has a final concentration of 0.1-10 v/v %, preferably 0.5-5 v/v % in the qPCR reaction liquid, for example, 1 v/v %, 2 v/v %, 3 v/v %, 4 v/v %, or 5 v/v %, more preferably, a final concentration of 3 v/v %.

In the present invention, the tetramethylammonium chloride has a final concentration of 10-100 mM, preferably 20-80 mM in the qPCR reaction liquid, for example, 20 mM, 40 mM, 60 mM, or 80 mM, more preferably, a final concentration of 35 mM.

In a second aspect, the present invention provides a qPCR reaction liquid, which contains the foregoing composition.

Further, the qPCR reaction liquid further comprises a sample, for example, a nucleic acid-extracted sample and/or a non-nucleic acid-extracted sample.

Further, the qPCR reaction liquid further comprises a primer and a probe for qPCR.

Still further, the qPCR reaction liquid further comprises a dNTP, a DNA polymerase, and a PCR buffer.

In the definition of the present invention, the term "qPCR reaction liquid" refers to a mixture capable of detecting a nucleic acid using fluorescence quantitative PCR.

In a particular embodiment, the qPCR reaction liquid comprises the foregoing composition, a primer and a probe, a dNTP, a DNA polymerase, and a PCR buffer.

In a third aspect, the present invention provides a use of the foregoing composition in improvement of qPCR detection performance, wherein advantageously, the improvement refers to improvement of performance of sensitivity, specificity, and/or interference resistance.

In the definition of the present invention, the term "detection performance" mainly refers to sensitivity, specificity, and interference resistance.

In a fourth aspect, the present invention provides a method for preparing a qPCR reaction liquid, the method comprising a step of mixing a sample with a reaction buffer and the foregoing composition.

The reaction buffer comprises, for example, a dNTP, a DNA polymerase, and a PCR buffer. Further, a primer and a probe may be comprised.

The use of the composition of the present invention can improve the sensitivity, specificity, and interference resistance of fluorescence quantitative PCR, and the concentration of the composition of the present invention used can further improve the sensitivity, specificity, and interference resistance of the fluorescent quantitative PCR. In particular, in the case of complex clinical examination, improving the detection performance can better provide molecular evidence for disease diagnosis and make adequate preparation for disease prevention and control, and can control infection sources for infectious and harmful infectious diseases in a timely manner, so as to block virus pandemics and outbreaks.

DETAILED DESCRIPTION

Figure 1:
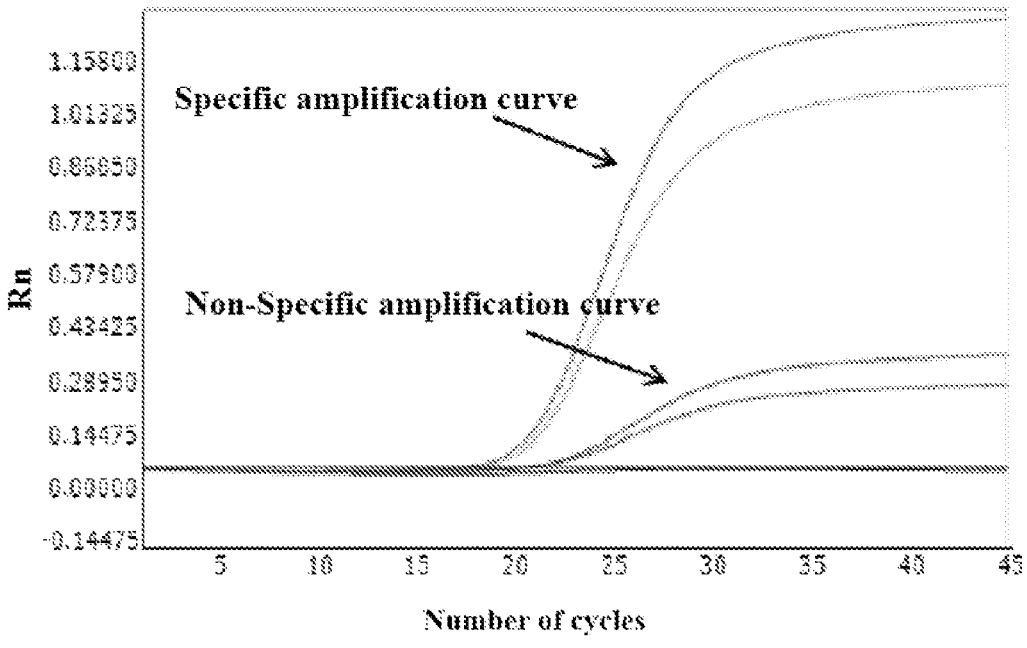
FIG. 1 is a graph showing amplification results in the absence of the composition of the present invention, using the same set of primer and probe for specific amplification of rs7412A in the presence of an APOE gene rs7412A/C template.
Figure 2:
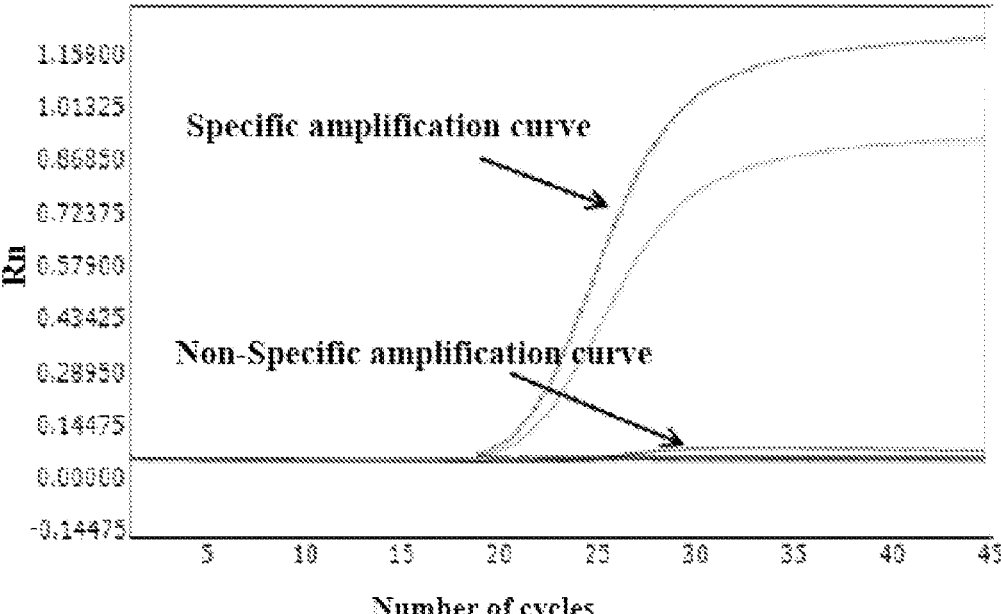
FIG. 2 is a graph showing amplification results in the presence of the composition of the present invention, using the same set of primer and probe for specific amplification of rs7412A in the presence of an APOE gene rs7412A/C template at the same concentration.

The present invention will be elaborated in detail below in combination with particular embodiments and examples, and advantages and various effects of the present invention will be more clearly presented therefrom. It should be understood by those skilled in the art that these particular embodiments and examples are used to describe the present invention, but not to limit the present invention.

EXAMPLE 1

Interference Resistance Performance of Different Compositions of the Present Invention in HCV Detection In a process of clinical application, a substance, such as SDS, bilirubin, and triglyceride, that causes PCR inhibition or interference is often added to a sample. Therefore, the investigation on the interference resistibility of PCR amplification reagents has become one of foci of performance of PCR reagents. In order to investigate the interference resistibility of the composition of the present invention in PCR amplification in a sample with an interferent, the composition of the present invention was applied to an HCV plasma sample with an interferent, and comparative detection was carried out with an HCV plasma sample without an interferent.

Comparative detection was performed on a low-concentration HCV sample (about 500 IU/mL) with an interference factor which was hemoglobin at a concentration of 2 g/dL. The detection scheme was to repeat detection on the sample ten times under each condition, and compare the detection repeatability and the detection rate. The detection method employed for the sample was a direct amplification method of a sample without nucleic acid extraction of 10 μL sample+10 μL nucleic acid releasing agent+30 μL PCR reaction liquid. Different combinations refer to combinations containing different compositions in a PCR reaction liquid. As shown in Table 1, "+" indicates that the component was added, and "–" indicates that the component was not added (after all ingredients were added to the qPCR reaction liquid, the ingredients had the following final concentrations: bovine serum albumin, 80 μg/mL; dithiothreitol, 3 mM; sorbitol, 4 w/v %; betaine, 0.8 mol/L; ammonium sulfate, 10 mM; formamide, 3 v/v %; and tetramethylammonium chloride, 35 mM).

TABLE 1

Effects of different compositions of the present invention on interference resistibility

| | BSA | DTT | Sorbitol | Betaine | Ammonium sulfate | Formamide | TMAC |
|---|---|---|---|---|---|---|---|
| Combination 1 | – | + | + | + | + | + | + |
| Combination 2 | + | – | + | + | + | + | + |
| Combination 3 | + | + | – | + | + | + | + |
| Combination 4 | + | + | + | – | + | + | + |
| Combination 5 | + | + | + | + | – | + | + |
| Combination 6 | + | + | + | + | + | – | + |
| Combination 7 | + | + | + | + | + | + | – |
| Combination 8 | + | + | + | + | + | + | + |
| Combination 9 | – | – | – | – | – | – | – |

TABLE 2

| | Combi-<br>nation | Combi-<br>nation 1 | Combi-<br>nation 2 | Combi-<br>nation 3 | Combi-<br>nation 4 | Combi-<br>nation 5 | Combi-<br>nation 6 | Combi-<br>nation 7 | Combi-<br>nation 8 | Combi-<br>nation 9 |
|---|---|---|---|---|---|---|---|---|---|---|
| Positive<br>rate | 7/10 | 8/10 | 6/10 | 8/10 | 7/10 | 6/10 | 7/10 | 10/10 | 0/10 | |

*Detection rates in low-concentration HCV samples with an inhibitor by different compositions*

According to the results in Table 2, the improvement of the detection capability by the compositions of the present invention differed to a certain extent among the low-concentration samples with the inhibitor. For the combination (Combination 8) containing all the ingredients, all of the 10 low-concentration samples were detected. At the same time, for the combination (Combination 9) not containing any component of the present invention, none of the 10 samples was detected. Therefore, the composition of the present invention had obvious advantages regarding the inhibition resistibility in the detection of low-concentration HCV samples. The different compositions of the present invention all had a positive effect on the improvement of the interference resistance.

EXAMPLE 2

Interference Resistance Performance of Different Compositions of the Present Invention for Detection of COVID-19 Viruses Comparative detection was performed on a low-concentration COVID-19 virus (hereinafter referred to as novel tion on the sample ten times under each condition, and compare the detection repeatability and the detection rate. The detection method employed for the sample was an amplification method of 10 μL interference sample+10 nucleic acid releasing agent+1 μL novel coronavirus nucleic acid sample+30 μL PCR reaction liquid, to investigate the influence on novel coronavirus nucleic acid amplification effects under different conditions. Different combinations refer to combinations containing different compositions in a PCR reaction liquid. As shown in Table 3, "+" indicates that the component was added, and "−" indicates that the component was not added (after all ingredients were added to the qPCR reaction liquid, the ingredients had the following final concentrations: bovine serum albumin, 80 μg/mL; dithiothreitol, 3 mM; sorbitol, 4 w/v %; betaine, 0.8 mol/L; ammonium sulfate, 10 mM; formamide, 3v/v %; and tetramethylammonium chloride, 35 mM). At the same time, the scheme adopted two control combinations as follows, Control 1: an interference-free sample (replaced with TE), a PCR reaction liquid without additive components; and Control 2: an interference-free sample (replaced with TE), a PCR reaction liquid with additive components.

TABLE 3

Effects of omission of different components in the present invention on interference resistibility and detection limit

| | BSA | DTT | Sorbitol | Betaine | Ammonium sulfate | Formamide | TMAC |
|---|---|---|---|---|---|---|---|
| Combination 1 | / | / | + | + | + | + | + |
| Combination 2 | / | + | + | / | + | + | + |
| Combination 3 | + | + | / | + | / | + | + |
| Combination 4 | / | + | + | / | + | + | + |
| Combination 5 | + | + | + | + | / | + | / |
| Combination 6 | + | + | / | / | + | + | + |
| Combination 7 | + | + | + | + | + | / | / |
| Combination 8 | + | / | + | + | + | / | + |
| Combination 9 | + | + | + | + | + | + | + |

TABLE 4

Detection rates of low-concentration novel coronavirus samples with an inhibitor by using different combinations

| | Combi-<br>nation | Combi-<br>nation 1 | Combi-<br>nation 2 | Combi-<br>nation 3 | Combi-<br>nation 4 | Combi-<br>nation 5 | Combi-<br>nation 6 | Combi-<br>nation 7 | Combi-<br>nation 8 | Combi-<br>nation 9 | Control 1 | Control 2 |
|---|---|---|---|---|---|---|---|---|---|---|---|---|
| Positive<br>rate | 5/10 | 6/10 | 6/10 | 5/10 | 5/10 | 6/10 | 6/10 | 8/10 | 10/10 | 10/10 | 10/10 | | coronavirus or 2019-nCoV) nucleic acid sample (1000 copies/mL) with an interference factor. The interference sample was a respiratory oropharyngeal swab sample with obvious turbid deposits. The detection scheme was to repeat detec- According to the results in Table 4, the improvement of the detection capability by the compositions of the present invention differed to a certain extent among the low concentration samples with the inhibitor. For the combination (Combination 9) containing all the ingredients, all of the 10 low-concentration samples were detected. The different compositions of the present invention all had a positive effect on the improvement of the interference resistance. Compared with the two control tests (Control 1 and Control 2) where both the controls were samples without an inhibition effect, only the pure nucleic acids were amplified and detected, and both were detected positive. With the additive components (Combination 9) adopted in Combination 9 of the present invention, the samples were also all detected positive.

EXAMPLE 3

Use of the Composition of the Present Invention in Improvement of Interference Resistance Performance of HCV Detection A composition of the present invention containing 7 components (bovine serum albumin, 80 µg/ml; dithiothreitol, 3 mM; sorbitol, 4 w/v %; betaine, 0.8 mol/L; ammonium sulfate, 10 mM; formamide, 3 v/v %; and tetramethylammonium chloride, 35 mM) was applied to an HCV plasma sample with an interferent, and comparative detection was carried out with an HCV plasma sample without an interferent. At the same time, for comparison, a PCR amplification reagent without the composition of the present invention was used as a control component, and was also added to HCV plasma samples with an interferent and without an interferent for comparative detection. Direct sample detection was carried out, and the method employed was a method of direct amplification performed on a sample with a total volume of 50 µL in which a sample: a sample release agent: a qPCR reaction liquid=10:10:30 (v/v). As this method employed direct sample amplification without nucleic acid extraction, the interference resistibility of the amplification reagent against the interference and inhibition effects in the sample was investigated in wider dimensions. The preparation method of the interference sample, the experimental comparison scheme, and the PCR amplification procedure used in the experimental process of this experimental scheme are shown in Table 5-7 below:

TABLE 5

Components and preparation method of interferent samples

| Sample No. | Interferent | Concentration | Notes |
|---|---|---|---|
| Interference sample 1 | Triglyceride | 3 g/dL | Preparation method of each interference sample: various interferents:plasma sample = 9:1, v/v |
| Interference sample 2 | Bilirubin | 100 mg/dL | |

TABLE 5-continued

Components and preparation method of interferent samples

| Sample No. | Interferent | Concentration | Notes |
|---|---|---|---|
| Interference sample 3 | Hemoglobin | 2 g/dL | |
| Interference sample 4 | IgG | 40 g/L | |
| Control sample | — | — | Plasma sample |

TABLE 6

Experimental comparison scheme for interference resistibility testing

| | Scheme of the present invention | Control scheme |
|---|---|---|
| Forward primer amount | 10 pmol | |
| Reverse primer amount | 10 pmol | |
| Probe amount | 5 pmol | |
| $Mg^{2+}$ | 2 pmol | |
| dNTP (U) | 2 pmol | |
| Enzyme mix | 4 µL | |
| Composition | 0.125 µL | 0 |
| PCR buffer | 23.625 µL | 23.5 µL |
| Nucleic acid amount | 20 µL | |
| Total reaction volume | 50 µL | |

TABLE 7

Experiments of testing interference resistibility for direct amplification of HCV samples

| Step | Temperature | Time | Number of cycles |
|---|---|---|---|
| Reverse transcription | 50° C. | 30 min | 1 |
| Pre-denaturation | 95° C. | 1 min | 1 |
| Denaturation | 95° C. | 15 sec | 45 |
| Annealing, extension, and fluorescence collection | 60° C. | 30 sec | |

In order to verify the amplification effect of the composition of the present invention in the interference sample, the composition was added to a PCR amplification reagent without the composition of the present invention, and a comparison test was carried out with a PCR amplification reagent without the composition of the present invention. Comparison of the measured Ct values of the samples was investigated. The Ct value was negatively correlated with the amplification efficiency, i.e., the larger the Ct value, the lower the amplification efficiency.

TABLE 8

Experiments of testing interference resistibility for direct amplification of HCV samples

| | Interference sample 1 | | Interference sample 2 | | Interference sample 3 | | Interference sample 4 | | Control sample | |
|---|---|---|---|---|---|---|---|---|---|---|
| Comparison results of nucleic acid extraction-free amplification of high-concentration HCV samples | | | | | | | | | | |
| Scheme of the present invention | 32.42 | 32.46 | 32.59 | 31.76 | 31.77 | 30.92 | 31.83 | 32.74 | 29.78 | 30.08 |
| Control scheme | 37.84 | 38.18 | No Ct | No Ct | No Ct | No Ct | 36.74 | 37.12 | 30.29 | 30.83 |

TABLE 8-continued

| | | | | | | | | | | |
|---|---|---|---|---|---|---|---|---|---|---|
| Comparison results of nucleic acid extraction-free amplification of medium/low-concentration HCV samples | | | | | | | | | | |
| Scheme of the present invention | 35.58 | 36.37 | 36.00 | 36.49 | 36.29 | 35.97 | 36.83 | 36.34 | 35.19 | 35.42 |
| Control scheme | No Ct | No Ct | No Ct | No Ct | No Ct | No Ct | No Ct | No Ct | 36.43 | 36.64 |

The above experiments showed that in the direct amplification test of the nucleic acid extraction-free sample, the composition of the present invention had a significantly improved interference resistibility against common interferents in serum samples. No matter whether the sample was a high-concentration or a medium/low-concentration HCV sample, there was no significant difference in the amplification efficiency between the interference sample with an interference factor and the control sample without the interference factor. However, compared with the control amplification reagent without the composition of the present invention, in the sample with the interference factor added, in the high-concentration HCV sample, for the sample containing the triglyceride and the IgG, the amplification efficiency was significantly decreased (the amplification Ct value was negatively correlated with the amplification efficiency, i.e., the larger the Ct value, the lower the amplification efficiency. No Ct means no amplification.). For the interference samples containing the bilirubin and the hemoglobin, the control reagent could not achieve the effect of an amplification test. For the low/medium-concentration HCV samples with lower concentrations, none of the interference samples could be amplified. This control experiment showed that the composition of the present invention had a significantly improved interference resistibility for qPCR amplification, especially in a sample lysis amplification technology that does not require nucleic acid extraction or purification.

EXAMPLE 4

Use of the Composition of the Present Invention in Improvement of Sensitivity of HCV Detection In order to evaluate the nucleic acid detection performance of the composition of the present invention containing all 7 ingredients (all the ingredients had the following final concentrations after being added to a qPCR reaction liquid: bovine serum albumin, 80 µg/mL; dithiothreitol, 3 mM; sorbitol, 4 w/v %; betaine, 0.8 mol/L; ammonium sulfate, 10 mM; formamide, 3 v/v %; and tetramethylammonium chloride, 35 mM) in emergency situations, a nucleic acid amplification reagent with the composition of the present invention was comparatively analyzed with a commercial reagent without the composition of the present invention. The comparison method adopted was gradual gradient dilution of a clinically diagnosed positive hepatitis C virus (HCV) sample, i.e., 10-fold dilution (1:9, v/v), 100-fold dilution (1:99, v/v), and 1000-fold dilution (1:999, v/v). A comparative test was carried out by using 10 µL nucleic acid releasing agent+10 µL HCV sample+30 µL PCR reaction liquid. The real-time fluorescent quantitative PCR (Real-time qPCR) amplification test procedure was as shown in Table 9:

TABLE 9

Amplification test procedure for HCV samples employed in the present invention

| Step | Temperature | Time | Number of cycles |
|---|---|---|---|
| Reverse transcription | 50° C. | 30 min | 1 |
| Pre-denaturation | 95° C. | 1 min | 1 |
| Denaturation | 95° C. | 15 sec | 45 |
| Annealing, extension, and fluorescence collection | 60° C. | 30 sec | |

The comparison results in Table 10 showed that for the composition of the present invention in the PCR amplification system of the present invention, the sensitivity aspect of the RT-PCR was significantly improved. The detection capability of the kit was negatively correlated with the cycle threathold (Ct) value. That is, the smaller the Ct value at the same concentration, the higher the detection capability; the larger the Ct value, the lower the detection capability. No Ct means no amplification. The composition of the present invention had a significant improvement in the detection capability for nucleic acids. The composition had a significantly improved detection capability for low-concentration nucleic acids as compared with the results of the control groups for the composition of the present invention, and had a significantly improved detection capability for clinically low-concentration samples. The use of the PCR additive components in the present invention could significantly improve the sensitivity and interference resistance of hepatitis C virus (HCV) detection, and could achieve timely and rapid diagnosis of diseases.

TABLE 10

Effects of the composition of the present invention on Ct values of nucleic acid amplification

| | PCR reaction liquid with the composition of the present invention | Commercial PCR reaction liquid |
|---|---|---|
| HCV sample | 26.64 | 28.09 |
| HCV sample diluted 10x | 29.89 | 32.21 |
| HCV sample diluted 100x | 33.11 | 35.83 |
| HCV sample diluted 1000x | 36.32 | No Ct |

EXAMPLE 5

Use of the Composition of the Present Invention in Improvement of Interference Resistance Performance of Novel Coronavirus Detection In order to prove the application of the composition of the present invention containing all 7 ingredients (after all the ingredients were added to a qPCR reaction liquid, the ingredients had the following final concentrations: bovine serum albumin, 80 µg/mL; dithiothreitol, 3 mM; sorbitol, 4 w/v %; betaine, 0.8 mol/L; ammonium sulfate, 10 mM;

formamide, 3 v/v %; and tetramethylammonium chloride, 35 mM) in the novel coronavirus detection, and the sampling method of the novel coronavirus is using an oropharyngeal swab/nasopharyngeal swab and storing the sample in a preservation solution for detection. For comparative verification to verify the interference resistibility of the composition of the present invention in the detection of novel coronavirus nucleic acids, the comparison scheme was to add 1 μL of a novel coronavirus nucleic acid at a concentration of about 1000 copies/mL into PCR Mastermix prepared, and at the same time add 10 μL of a sample with an inhibition effect and 10 μL of a nucleic acid releasing agent, to construct a reaction system with a total volume of 50 so as to verify the interference resistibility of the novel coronavirus detection system in the amplification system. For comparative verification, both a control group and a blank group were used for the verification, specifically as shown in Table 11. Amplification tests were performed using the amplification procedure in Table 7 for all conditions.

TABLE 11

Comparison of the interference resistibility of the scheme of the present invention in 2019-nCoV nucleic acid detection systems

| | Scheme of the present invention | Control scheme | Blank scheme |
|---|---|---|---|
| Forward primer amount | | 10 pmol | |
| Reverse primer amount | | 10 pmol | |
| Probe amount | | 5 pmol | |
| Mg$^{2+}$ | | 2 pmol | |
| dNTP (T) | | 2 pmol | |
| Enzyme mix | | 4 μL | |
| Composition of the present invention | 0.15 μL | / | / |
| Nucleic acid | | 1 μL | |
| PCR buffer | 23.65 μL | 23.5 μL | 23.5 μL |
| Nucleic acid releasing agent | 10 μL | 10 μL | 10 μL |
| Sample with an inhibition effect | 10 μL | 10 μL | / |
| Sample without an inhibition effect | / | / | 10 μL |
| Total reaction volume | | 50 μL | |

TABLE 12

Improvement of interference resistibility for 2019-nCoV nucleic acid detection by the scheme of the present invention

| Combination | Scheme of the present invention | Control scheme | Blank scheme |
|---|---|---|---|
| Positive rate | 10/10 | 2/10 | 10/10 |

This experimental scheme aimed to verify the effect of the composition of the present invention on the interference resistibility of the 2019-nCoV detection system. It can be seen from the comparison results in Table 12 that in the nucleic acid detection reagent with the composition of the present invention added thereto, in the presence of a sample with an obvious inhibition effect, 2019-nCoV nucleic acids at a concentration of about 1000 copies/mL were all detected. Under the same condition, in the control group without the composition of the present invention added, in the presence of a sample with an inhibition effect, the positive detection rate of 2019-nCoV nucleic acids at the same concentration was much lower, only 2/10. In contrast, in the absence of the composition of the present invention, in the presence of a sample without an inhibition effect, all the 2019-nCoV nucleic acids at the same concentration were detected positive. Therefore, it was found that the sample with a strong inhibition effect had a very obvious effect on the amplification system, and could strongly inhibit the amplification effect of the commercial control system, but the composition of the present invention could significantly improve the interference resistibility of the detection reagent components.

EXAMPLE 6

Use of the Composition of the Present Invention in Improvement of Sensitivity of Novel Coronavirus Detection In order to evaluate the nucleic acid detection performance of the composition of the present invention containing all 7 ingredients (after all the ingredients were added to a qPCR reaction liquid, the ingredients had the following final concentrations: bovine serum albumin, 80 μg/mL; dithiothreitol, 3 mM; sorbitol, 4 w/v %; betaine, 0.8 mol/L; ammonium sulfate, 10 mM; formamide, 3 v/v %; and tetramethylammonium chloride, 35 mM) in emergency situations, a nucleic acid amplification reagent with the composition of the present invention was comparatively analyzed with a commercial reagent without the composition of the present invention. The comparison method adopted was gradual gradient dilution of a clinically diagnosed positive novel coronavirus (2019-nCoV) nucleic acid sample, i.e., 10-fold dilution (1:9, v/v), 100-fold dilution (1:99, v/v), 1000-fold dilution (1:999, v/v), and 10000-fold dilution (1:9999, v/v). The comparative test was carried out by using 45 μL PCR reaction liquid+5 μL nucleic acid sample. The real-time fluorescent quantitative PCR (Real-time qPCR) amplification test procedure was as shown in Table 13:

TABLE 13

Amplification test procedure for 2019-nCoV nucleic acid employed in the present invention

| Step | Temperature | Time | Number of cycles |
|---|---|---|---|
| Reverse transcription | 50° C. | 30 min | 1 |
| Pre-denaturation | 95° C. | 1 min | 1 |
| Denaturation | 95° C. | 15 sec | 45 |
| Annealing, extension, and fluorescence collection | 60° C. | 30 sec | |

The comparison results in Table 14 showed that for the composition of the present invention in the PCR amplification system of the present invention, the sensitivity of RT-PCR was significantly improved. The detection capability of the kit was negatively correlated with the cycle threathold (Ct) value. That is, the smaller the Ct value at the same concentration, the higher the detection capability; the larger the Ct value, the lower the detection capability. No Ct means no amplification. The composition of the present invention had a significant improvement in the detection capability for nucleic acids. The composition had a significantly improved detection capability for low-concentration nucleic acids as compared with the results of the control groups for the composition of the present invention, and had a significantly improved detection capability for clinically low-concentration samples.

TABLE 14

| Effects of the composition of the present invention on Ct values of nucleic acid amplification | | |
|---|---|---|
| | PCR reaction liquid with the composition of the present invention | Commercial PCR reaction liquid |
| Nucleic acid diluted 10x | 28.64 | 29.89 |
| Nucleic acid diluted 100x | 31.89 | 33.32 |
| Nucleic acid diluted 1000x | 35.07 | 37.03 |
| Nucleic acid diluted 10000x | 38.34 | No Ct |

By improving the sensitivity and interference resistance in the detection of the novel coronavirus 2019-nCoV, infection sources can be controlled in a timely manner, and virus pandemics and outbreaks can be blocked.

EXAMPLE 7

Use of the Composition of the Present Invention in Improvement of Detection Specificity In order to evaluate the effect of the composition of the present invention containing 7 components (after all the ingredients were added to a qPCR reaction liquid, the ingredients had the following final concentrations: bovine serum albumin, 80 µg/mL; dithiothreitol, 3 mM; sorbitol, 4 w/v %; betaine, 0.8 mol/L; ammonium sulfate, 10 mM; formamide, 3 v/v %; and tetramethylammonium chloride, 35 mM) for detection specificity, the composition of the present invention was added to a PCR amplification system, and a comparative study was carried out with a PCR amplification system without the composition of the present invention. In order to highlight the effect of the composition, the same primer and probe sequence and concentration and the same nucleic acid concentration were used for amplification tests. In terms of verifying the detection specificity, the composition of the present invention was applied to analysis of human genome polymorphism (human APOE gene r57412) for specificity comparison of amplification tests. The experimental design was as follows:

TABLE 15

| Comparison test of specific amplification based on polymorphism analysis of human APOE gene rs7412 | | |
|---|---|---|
| | Amplification scheme of the present invention | Control scheme |
| Forward primer sequence | 5'-GCGGACATGGAGGACGTG-3' (SEQ ID NO: 1) | |
| Reverse primer sequence | 5'-GCTGCCCATCTCCTCCATC-3' (SEQ ID NO: 2) | |
| Taqman probe sequence | 5'-CTTCTGCAGGTCATCGGCATCGC-3' (SEQ ID NO: 3) | |
| Forward primer amount | 10 pmol | |
| Reverse primer amount | 10 pmol | |
| Probe amount | 5 pmol | |
| Mg$^{2+}$ | 2 pmol | |
| dNTP (T) | 2 pmol | |

TABLE 15-continued

| Comparison test of specific amplification based on polymorphism analysis of human APOE gene rs7412 | | |
|---|---|---|
| | Amplification scheme of the present invention | Control scheme |
| Enzyme mix | 4 µL | |
| Composition of the present invention | 0.15 µL | 0 |
| PCR buffer | 33.65 µL | 33.5 µL |
| Nucleic acid amount | 5 µL | |
| Total reaction volume | 50 µL | |

TABLE 16

| qPCR amplification test procedure for human gene APOE polymorphism analysis | | | |
|---|---|---|---|
| Step | Temperature | Time | Number of cycles |
| UNG enzyme | 50° C. | 5 min | 1 |
| Thermal activation | 95° C. | 1 min | 1 |
| Denaturation | 95° C. | 15 sec | 45 |
| Annealing, extension, and fluorescence collection | 60° C. | 30 sec | |

Human genome polymorphism analysis has a very high requirement for amplification specificity. It can be seen from the results of FIG. 1 of the present experimental design that in the conventional qPCR reaction system without the composition of the present invention, the probe for detecting the APOE gene rs7412A had an obvious non-specific amplification curve in the presence of an APOE gene rs7412C template. Although the non-specific amplification curve had a low curve fluorescence intensity due to a weak binding force, it still had an adverse effect on result determination. After the addition of the composition of the present invention, the non-specific amplification of the detection system was obviously improved. The presence of the APOE gene rs7412C template had no effect on the detection at all, and there was no amplification signal at all. This control test showed that even in the case of a very small amount, the composition of the present invention had an obvious inhibition capability against non-specific amplification of qPCR, and significantly improved the qPCR specificity.

REFERENCE TO AN ELECTRONIC SEQUENCE LISTING

The contents of the electronic sequence listing (CU707SequenceListing.xml; Size: 4,076 bytes; and Date of Creation: Sep. 27, 2022) is herein incorporated by reference in its entirety.

What is claimed is:

1. A composition for improving qPCR detection performance, consisting of the following components: bovine serum albumin, sorbitol, ammonium sulfate, formamide, and tetramethylammonium chloride, and at least one of dithiothreitol and betaine;

wherein components in the composition are formulated to have the following final concentrations after being added to a qPCR reaction liquid: bovine serum protein, 10-150 µg/ml; dithiothreitol, 1-10 mM; sorbitol, 1-10 w/v %, betaine, 0.5-4 mol/L; ammonium sulfate, 2-50 mM; formamide, 0.1-10 v/v %; and tetramethylammonium chloride, 10-100 mM.

2. The composition according to claim 1, wherein the composition comprises bovine serum albumin, dithiothreitol, sorbitol, ammonium sulfate, formamide, and tetramethylammonium chloride.

3. The composition according to claim 1, wherein the composition comprises bovine serum albumin, sorbitol, betaine, ammonium sulfate, formamide, and tetramethylammonium chloride.

4. The composition according to claim 1, wherein the composition comprises bovine serum albumin, dithiothreitol, sorbitol, betaine, ammonium sulfate, formamide, and tetramethylammonium chloride.

5. The composition according to claim 1, wherein the components in the composition are formulated to have the following final concentrations after being added to the qPCR reaction liquid: bovine serum protein, 80-120 µg/ml; dithiothreitol, 2-8 mM; sorbitol, 4-6 w/v %; betaine, 0.6-1 mol/L; ammonium sulfate, 8-15 mM; formamide, 0.5-5 v/v %; and tetramethylammonium chloride, 20-80 mM.

6. The composition according to claim 1, wherein the components in the composition are formulated to have the following final concentrations after being added to the qPCR reaction liquid: bovine serum albumin, 80 µg/mL; dithiothreitol, 3 mM; sorbitol, 4 w/v %; betaine, 0.8 mol/L; ammonium sulfate, 10 mM; formamide, 3 v/v %; and tetramethylammonium chloride, 35 mM.

7. A qPCR reaction liquid, comprising the composition of claim 1.

8. The qPCR reaction liquid according to claim 7, comprising a sample.

9. The qPCR reaction liquid according to claim 8, wherein the sample comprises a nucleic acid-extracted sample and/or a non-nucleic acid-extracted sample.

10. The qPCR reaction liquid according to claim 7, further comprises a primer and a probe, a dNTP, a DNA polymerase, and a PCR buffer.

11. A method for improving detection performance of qPCR, comprising adding the composition of claim 1 to a qPCR reaction system.

12. A method for improving the detection performance of qPCR, comprising adding the qPCR reaction liquid of claim 7 to a qPCR reaction system.

13. A method for preparing a qPCR reaction liquid, wherein the method comprising a step of mixing a sample with a reaction buffer and the composition of claim 1.

14. The method according to claim 13, wherein the reaction buffer comprises a dNTP, a DNA polymerase, and a PCR buffer.

15. The method according to claim 13, wherein the reaction buffer further comprises a primer and a probe.

\* \* \* \* \*